United States Patent
Di Maiuta et al.

(10) Patent No.: US 9,345,241 B2
(45) Date of Patent: May 24, 2016

(54) COMPOSITION HAVING BIOCIDE ACTIVITY FOR AQUEOUS PREPARATIONS

(71) Applicants: Nicola Di Maiuta, Zuchwil (CH); Patrick Schwarzentruber, Habsburg (CH); Matthias Buri, Rothrist (CH); Patrick Arthur Charles Gane, Rothrist (CH)

(72) Inventors: Nicola Di Maiuta, Zuchwil (CH); Patrick Schwarzentruber, Habsburg (CH); Matthias Buri, Rothrist (CH); Patrick Arthur Charles Gane, Rothrist (CH)

(73) Assignee: Omya International AG, Oftringen (CH)

( * ) Notice: Subject to any disclaimer, the term of this patent is extended or adjusted under 35 U.S.C. 154(b) by 532 days.

(21) Appl. No.: 13/734,016

(22) Filed: Jan. 4, 2013

(65) Prior Publication Data

US 2013/0123369 A1 May 16, 2013

Related U.S. Application Data

(62) Division of application No. 12/736,355, filed as application No. PCT/EP2009/053903 on Apr. 1, 2009, now Pat. No. 9,107,406.

(60) Provisional application No. 61/124,637, filed on Apr. 18, 2008, provisional application No. 61/207,005, filed on Feb. 6, 2009.

(30) Foreign Application Priority Data

Apr. 11, 2008 (EP) .................................. 08154448
Jan. 30, 2009 (EP) .................................. 09151791

(51) Int. Cl.
*A01N 59/00* (2006.01)
*A01N 35/02* (2006.01)
*A01N 25/00* (2006.01)
*C02F 1/50* (2006.01)

(52) U.S. Cl.
CPC ................ *A01N 25/00* (2013.01); *A01N 35/02* (2013.01); *A01N 59/00* (2013.01); *C02F 1/50* (2013.01)

(58) Field of Classification Search
None
See application file for complete search history.

(56) References Cited

U.S. PATENT DOCUMENTS

| | | |
|---|---|---|
| 3,983,252 A | 9/1976 | Buchalter |
| 4,655,815 A | 4/1987 | Jakubowski |
| 5,278,248 A | 1/1994 | Egraz et al. |
| 5,496,398 A | 3/1996 | Drew et al. |
| 6,391,150 B1 | 5/2002 | Berger et al. |
| 8,329,063 B2 | 12/2012 | Beilfuss et al. |
| 2001/0009682 A1 | 7/2001 | Whiteley |
| 2005/0136118 A1 | 6/2005 | Wu et al. |
| 2006/0111410 A1 | 5/2006 | Wachtler et al. |

FOREIGN PATENT DOCUMENTS

| | | |
|---|---|---|
| EP | 1547621 A2 | 6/2005 |
| EP | 1623725 A2 | 2/2006 |
| EP | 1661587 A1 | 5/2006 |
| GB | 1443786 A | 7/1976 |
| WO | 02052941 A1 | 7/2002 |
| WO | 2004040979 A1 | 5/2004 |
| WO | 2006079911 A1 | 8/2006 |

OTHER PUBLICATIONS

The International Search Report for PCT Application No. PCT/EP2009/053903.
The Written Opinion of the International Searching Authority for PCT Application No. PCT/EP2009/053903.

*Primary Examiner* — Irene Marx
(74) *Attorney, Agent, or Firm* — Amster, Rothstein & Ebenstein LLP

(57) ABSTRACT

The present invention refers to a process for bacterial stabilizing aqueous preparations like e.g. calcium carbonate slurries and a composition which can be used for the biocidal treatment of such aqueous preparations.

16 Claims, No Drawings

COMPOSITION HAVING BIOCIDE ACTIVITY FOR AQUEOUS PREPARATIONS

CROSS-REFERENCE TO RELATED APPLICATIONS

The present application is a divisional of U.S. application Ser. No. 12/736,355, filed Apr. 1, 2009, which is a U.S. National Phase of PCT Application No. PCT/EP2009/053903, filed Apr. 1, 2009, which claims the benefit of EP Application No. 01854448.8, filed Apr. 11, 2008, U.S. Provisional Application No. 61/124,637, filed Apr. 18, 2008, European Application No. 09151791.2, filed Jan. 20, 2009, and U.S. Provisional Application No. 61/207,005, filed Feb. 6, 2009, the contents of which are hereby incorporated herein by reference in their entirety.

FIELD OF THE INVENTION

The invention relates to a composition providing biocidal activity in aqueous preparations, like suspensions or dispersions and especially White Mineral Dispersions (WMD). The invention further relates to processes for bacterial stabilizing such aqueous preparations and to the use of biocidal activity effecting compounds.

BACKGROUND OF THE INVENTION

In practice, aqueous preparations and especially suspensions, dispersions or slurries of water-insoluble solids such as minerals, fillers or pigments are used extensively in the paper, paint, rubber and plastics industries as coatings, fillers, extenders and pigments for papermaking as well as aqueous lacquers and paints. For example, suspensions or slurries of calcium carbonate, talc or kaolin are used in the paper industry in large amounts as filler and/or as a component in the preparation of coated paper. Typical aqueous preparations of water-insoluble solids are characterized in that they comprise water, a water-insoluble solid compound and optionally further additives, such as dispersing agents, in the form of a suspension, a slurry or dispersion with a water-insoluble solid content of 1 to 80 wt.-% based on the total weight of the preparation. A typical aqueous preparation is a White Mineral Dispersion (WMD) having a solids content of 45 to 78 wt.-%. Water-soluble polymers and copolymers which may be used as e.g. dispersant and/or grinding aid in such preparation are, for example, described in U.S. Pat. No. 5,278,248.

The aforementioned aqueous preparations are often subject to contamination by microorganisms such as aerobic and anaerobic bacteria resulting in changes in the preparation properties such as changes in viscosity and/or pH, discolorations or reductions in other quality parameters, which negatively affect their commercial value. Therefore, the manufacturers of such aqueous preparations usually take measures for stabilizing the suspensions, dispersions or slurries. For example, it is known that aldehyde-releasing biocides reduce the growth and accumulation of such microorganisms in aqueous preparations and, thus, reduce the tendency of undesired alterations of these preparations, like viscosity changes or unpleasant odours.

For ensuring an acceptable microbiological quality of aqueous preparations, preservatives or biocides are used over the entire life cycle of the preparation (production, storage, transport, use). In the art, several approaches for improving the microbiological quality of aqueous preparations have been proposed. For example, EP 1 139 741 describes aqueous suspensions or dispersions of minerals, fillers and/or pigments, containing a microbiocidal agent in the form of a solution and derivatives of phenol in partially neutralized form. U.S. Pat. No. 5,496,398 relates to a process for the reduction of microorganisms in kaolin clay slurries by a combination of low temperature heat and reduced levels of a microbiocidal agent. WO 02/052941 describes biocide compositions for incorporation into paints, coating, plasters and plastics comprising at least one metal oxide and at least one metal salt. US 2006/0111410 mentions a mixture comprising 1,2-benzisothiazolinone (BIT) and tetramethylolacetylenediurea (TMAD) for protecting industrial materials and products against attack and destruction by microorganisms. Furthermore, it is suggested in the art to add formaldehyde-releasing substances to such aqueous preparations for improving the microbiological quality. For example, U.S. Pat. No. 4,655,815 mentions a antimicrobial composition comprising a formaldehyde donor. Furthermore, WO 2006/079911 describes a method of protection against microorganisms by increasing the OH$^-$ ion concentration of the suspension.

WO 2004/040979 A1 relates to synergic antimicrobial mixtures containing 1,2-benzisothiazolinon (BIT) and benzylhemiformal (BHF). The corresponding mixtures are used, for example, for slurries of pigments. WO 2004/040979 A1 is not concerned with the treatment of aqueous preparations containing strains of bacteria which are resistant to, tolerant to and/or degrade aldehyde-releasing biocides. EP 1 661 587 A1 relates to germicidal compositions including phthalaldehyde as an active ingredient. It is indicated in EP 1 661 587 A1 that carbonate salts and bicarbonate salts may enhance the germicidal efficacy of phthalaldehydes. However, EP 1 661 587 A1 is not concerned with the treatment of aqueous preparations containing strains of bacteria which are resistant to, tolerant to and/or degrade aldehyde-releasing biocides.

US 2001/0009682 A1 relates to disinfectant concentrates having improved biocidal activity which may contain an aldehyde such as glutaraldehyde, a glycol and a lithium based buffer. It is described in US 2001/0009682 A1 that the buffer is required to control the pH of both the concentrate and its dilutions within the desired biocidal effective range. Also US 2001/0009682 A1 is not concerned with the treatment of aqueous preparations containing strains of bacteria which are resistant to, tolerant to and/or degrade aldehyde-releasing biocides.

Because of the limited activity spectrum of several biocides, the efficacy of such biocides against bacteria is not always satisfactory if strains of bacteria are present which are resistant to, tolerant to and/or degrade such biocides, and, thus, the obtained action is in some cases insufficient to avoid microbially induced alteration of aqueous preparations.

Thus, there is still a need for adequate compositions providing sufficient biocidal activity in aqueous preparations such as suspensions, dispersions and slurries of water-insoluble solids in order to achieve a longer lasting and sufficient stabilization.

SUMMARY OF THE INVENTION

It is an objective of the present invention to provide a composition which provides an effective biocidal activity in aqueous preparations, such as dispersions, suspensions or slurries of water-insoluble solids containing strains of bacteria which are resistant to, tolerant to and/or degrade specific biocides. A further objective of the present invention is to provide a composition for reducing the growth and accumulation of microorganisms in aqueous preparations and, thus, reducing the tendency of alterations of these preparations and maintaining the desired viscosity and pH, the brilliance and colour and preventing bad odour. Another objective of the present invention is to provide a composition for reducing the growth and accumulation of microorganisms in aqueous preparations containing strains of bacteria which are resistant to, tolerant to and/or degrade specific biocides and, thus, reducing the tendency of alterations of these preparations and maintaining the desired viscosity and pH, the brilliance and colour and preventing bad odour. Another objective is to provide a composition or process for bacterial stabilizing and/or disinfecting and/or preserving and/or controlling of the microbial contamination of aqueous preparations. Even a further objective of the invention is to provide a composition which is easy to apply and distribute in aqueous preparations and which reduces or avoids the formation of aggregates or an increase of the viscosity or reduction of physical storage stability of the aqueous preparation.

These and other objectives of the present invention can be solved by a process and a composition as described in the present invention and defined in the claims.

DETAILED DESCRIPTION OF THE INVENTION

According to one aspect of the present application a process for bacterial stabilizing an aqueous preparation is provided, said preparation comprising at least one mineral and at least one strain of bacteria which is resistant to, tolerant to and/or degrade aldehyde-releasing and/or aldehyde-based biocides, wherein the process comprises the steps of:
(a) adding to the aqueous preparation one or more aldehyde-releasing and/or aldehyde-based biocides in an amount such that the total amount of aldehyde-releasing and/or aldehyde-based biocides in the aqueous preparation is from 250 ppm to 5000 ppm, calculated relative to the water in the preparation;
(b) adding at least one water soluble lithium compound to the aqueous preparation in an amount such that the total amount of solubilised lithium in the aqueous preparation is from 1000 to 3000 ppm, calculated relative to the weight of water in the preparation, where steps (a) and (b) may be carried out simultaneously, or separately in any order.

According to the present invention, said solubilised lithium is preferably in the form of lithium ions in water.

In accordance with the present invention, the at least one source of a water soluble lithium may be regarded as a biocidal activity effecting or biocidal activity inducing compound. When subsequently reference is made to a biocidal activity effecting compound, the at least one source of a water soluble lithium is meant.

In accordance with the present invention, an "aldehyde-releasing biocide" refers to a compound which is able to release mono- di-, and/or tri-aldehyde. Aldehyde-releasing biocides include, for example, (ethylenedioxy)dimethanol, which releases formaldehyde.

In accordance with the present invention, an "aldehyde-based biocide" refers to a biocide which has one or more aldehyde-group. Aldehyde-based biocides include, for example, formaldehyde, acetaldehyde, propionaldehyde, glutardialdehyde and glyoxal.

In the meaning of the present invention, a "biocidal activity effecting compound" is a compound which induces or effects biocidal activity (e.g. reduction or prevention of the growth and/or accumulation of microorganisms) in an aqueous preparation containing an "aldehyde-releasing and/or aldehyde-based biocide" in comparison to an aqueous preparation containing an "aldehyde-releasing and/or aldehyde-based biocide" but no such "biocidal activity effecting compound" (other than a content of dissolved lithium ions which may naturally be present in the aqueous preparation).

The amount of solubilised lithium in the aqueous preparation and the amount of aldehyde-releasing and/or aldehyde-based biocide in the aqueous preparation, i.e. the content or concentration of the lithium and the biocide(s) in the aqueous preparation, as specified herein corresponds to the amount which is necessary to achieve the inventive biocidal activity and the advantages of the present invention. Consequently, the solubilised lithium and the aldehyde-releasing and/or aldehyde-based biocide according to the present invention will be added at the beginning of the process in corresponding amounts in order to adjust the concentration required in the aqueous preparation. If necessary, an additional amount of the solubilised lithium and/or the aldehyde-releasing and/or aldehyde-based biocide may be added during the inventive stabilizing process in order to maintain the biocidal activity or the stabilizing effect. Said additional amount according to the present invention is to be selected such that the concentration of the solubilised lithium and/or the aldehyde-releasing and/or or aldehyde-based biocide is increased above the respective minimum amount specified herein but, at the same time, does not exceed the specified maximum amounts.

In the meaning of the present invention, bacteria which are "resistant" refer to bacteria having the ability to withstand the effects of said aldehyde-releasing biocides and/or aldehyde-based biocides when dosed in an amount such that the total amount of aldehyde-releasing biocides and/or aldehyde-based biocides in the aqueous preparation is from 250 ppm to 5000 ppm, calculated relative to the amount of water in the preparation. Such resistance evolves naturally via natural selection acting upon random mutation, but it can also be engineered by applying an evolutionary stress on a population.

In the meaning of the present invention, bacteria which are "tolerant" refer to bacteria having the ability to survive in the presence of said aldehyde-releasing biocides and/or aldehyde-based biocides without evolving a random mutation.

Bacteria which "degrade" said aldehyde-releasing biocides and/or aldehyde-based biocides in the meaning of the present invention correspond to bacteria having the ability to convert said biocides into inactive forms and/or smaller molecules, e.g. by utilizing these substrates as intermediates in their pathways.

According to the present invention, a "significant growth" of strains of bacteria which are resistant to, tolerant to and/or degrade said aldehyde-releasing and/or aldehyde-based biocides is observed if the difference, i.e. the growth of the bacteria is greater than the error associated with the measurement technique when tested within one-week and measured by plate-out on a plate count agar (PCA), where the plates are incubated at 30° C. and evaluated after 48 hours, according to the standard plate count method.

According to the present invention, the wording "bacterial stabilizing an aqueous preparation" means that no "significant growth" of strains of bacteria which are resistant to, tolerant to and/or degrade said aldehyde-releasing and/or aldehyde-based biocides is observed. Preferably, the stabilization leads to a reduction of the cfu/ml value (colony forming unit per milliliter) of the treated aqueous preparation to a value of less than $10^4$ cfu/ml, more preferably to a value of less than $10^3$ cfu/ml, and even more preferably to a value of less than $10^2$ cfu/ml.

According to the present invention, the lithium content in water can be evaluated by filtering off the solids in the suspension by membrane filtration (pore size of 0.2 microns) and measuring the lithium content in the filtrate by liquid chromatography.

According to the present invention, the content of the aldehyde-releasing and/or aldehyde-based biocides in water can be evaluated by HPLC (high pressure liquid chromatography). If necessary, the corresponding aldehyde-releasing and/or aldehyde-based biocide may be converted into a derivative before evaluating with HPLC.

A "slurry" in the meaning of the present invention is a suspension comprising insoluble minerals and water and optionally further additives. Slurries usually contain large amounts of solids and are more viscous and generally of higher density than the liquid from which they are formed.

The term "mineral" in the meaning of the present application encompasses natural or synthetic minerals, fillers and/or pigments, like calcium carbonate, talc, chalk, dolomite, mica, titanium dioxide, etc.

According to the present invention, the term "stabilizing an aqueous preparation" means that the number of bacteria is lowered by adding a biocidal composition such that the preparation remains stable.

The total solids content in the meaning of the present application corresponds to the residual weight of the preparation after drying for 3 hours at 105° C.

A "White Mineral Dispersion" (WMD) in the meaning of the present application is a mineral dispersion containing dry and/or wet ground natural calcium carbonate and/or dolomite and/or precipitated calcium carbonate in its aragonitic, calcitic or vateritic form, clay, such as kaolin and/or montmorilonite, and/or mica, and/or talc which provides improved properties, such as optical and/or mechanical properties to paper, paints and plastics.

"Ground calcium carbonate" (GCC) in the meaning of the present invention is a calcium carbonate obtained from natural sources, such as limestone, marble or chalk or dolomite, and processed through a treatment such as grinding, screening and/or fractionizing by wet and/or dry, for example by a cyclone or classifier.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water.

Furthermore, the present invention refers to the use of a composition comprising:
(a) one or more aldehyde-releasing and/or aldehyde-based biocides in an amount such that the total amount of aldehyde-releasing and/or aldehyde-based biocides in the aqueous preparation is from 250 ppm to 5000 ppm, calculated relative to the water in the preparation, and
(b) at least one source of a water soluble lithium compound in an amount such that the total amount of solubilised lithium, preferably in the form of lithium ions, in the aqueous preparation is from 1000 to 3000 ppm, calculated relative to the weight of water in the preparation;
as a biocidal composition in an aqueous preparation comprising strains of bacteria which are resistant to, tolerant to and/or degrade said aldehyde-releasing and/or aldehyde-based biocides in absence of lithium.

The present invention also refers to the use of lithium ions as biocidal activity effecting compound for bacterial stabilizing an aqueous preparation comprising an aldehyde-releasing and/or aldehyde-based biocide and strains of bacteria which are resistant to, tolerant to and/or degrade said aldehyde-releasing biocides and/or aldehyde-based biocides in absence of said lithium ions.

According to another aspect of the present invention, a composition providing biocidal activity in aqueous preparations is provided, wherein the composition comprises:
(a) one or more aldehyde-releasing and/or aldehyde-based biocides; and
(b) at least one source of a water soluble lithium compound; wherein the at least one source of a water soluble lithium compound is a polymeric salt of lithium, said polymer salt of lithium being preferably a homopolymer and/or copolymer of acrylic acid.

It is especially preferred to use the inventive composition in the process for bacterial stabilizing an aqueous preparation, i.e. to add said composition to the preparation.

With respect to the amounts of polymeric inorganic and/or organic salts of lithium and the aldehyde-releasing and/or aldehyde-based biocide contained in the composition, the skilled person knows how to adjust a suitable concentration or amount so that the contemplated concentrations in the final aqueous preparation can be achieved. For example, the weight ratio of the aldehyde-releasing and/or aldehyde-based biocide to the polymeric salt of lithium in the composition may be adjusted such that it allows for adjusting the concentration of aldehyde-releasing and/or aldehyde-based biocide to be from 250 ppm to 5000 ppm and the concentration of solubilised lithium resulting from the addition of the polymeric salt of lithium to be from 1000 ppm to 3000 ppm, calculated relative to the weight of water in the preparation, after adding said composition to an aqueous preparation.

When in the following reference is made to preferred embodiments or technical details of the inventive process for bacterial stabilizing aqueous preparations, it is to be understood that these preferred embodiments or technical details also refer to the inventive compositions and the inventive use of the compositions defined herein (as far as applicable). If, for example, it is set out that the inventive process preferably is carried out by using one or more aldehyde-releasing and/or aldehyde-based biocides being selected from the group consisting of formaldehyde-releasing biocides, acetaldehyde-releasing biocides and succinaldehyde-releasing biocides, also the inventive composition preferably comprises one or more aldehyde-releasing and/or aldehyde-based biocides being selected from the group consisting of formaldehyde-releasing biocides, acetaldehyde-releasing biocides and succinaldehyde-releasing biocides.

According to one preferred embodiment of the inventive process or composition, said solubilised lithium is in the form of lithium ions.

According to another preferred embodiment of the inventive process, the aldehyde-releasing and/or aldehyde-based biocide and said soluble lithium compound are added separately to the aqueous preparation.

According to yet another preferred embodiment of the inventive process, said soluble lithium compound may be added before said aldehyde-releasing and/or aldehyde-based biocide. In the alternative, it may especially be preferred according to the inventive process that said aldehyde-releasing and/or aldehyde-based biocide is added before said soluble lithium compound.

According to one especially preferred embodiment of the inventive process or composition, the aldehyde-releasing compound is selected from the group consisting of formaldehyde-releasing biocides, acetaldehyde-releasing biocides, succinaldehyde-releasing biocides, 2-propenal-releasing biocides and mixtures thereof, preferably from formaldehyde-releasing biocides, said formaldehyde-releasing biocides being preferably selected from the group comprising benzyl alcoholmono(poly)-hemiformal, ethylenglycolhemiformal, tetrahydro-1,3,4,6-tetrakis(hydroxylmethyl)imidazo

[4,5-d]imidazole-2,5(1H,3H)-dione (also commonly referred to as TetraMethylolAcetyleneDiurea TMAD) and mixtures thereof.

According to another especially preferred embodiment of the inventive process or composition, the aldehyde-based biocide is selected from the group comprising formaldehyde, acetaldehyde, glyoxal, glutaraldehyde, 2-propenal, phthalic dialdehyde and mixtures thereof, and preferably is formaldehyde, glutaraldehyde or mixtures thereof.

According to yet another preferred embodiment of the inventive process or composition, the aldehyde-releasing and/or aldehyde-based biocide is used together with other biocides selected from the group consisting of 5-chloro-2-methyl-2H-isothiazolin-3-one (CIT), 2-methyl-2H-isothiazolin-3-one (MIT) and mixtures thereof.

According to an especially preferred embodiment of the inventive process, the aldehyde-releasing and/or aldehyde-based biocide is added to the aqueous preparation in an amount of from 750 ppm to 4000 ppm, preferably in amount of from 1500 ppm to 3000 ppm, calculated relative to the water in the preparation.

Another preferred embodiment of the inventive process relates to the at least one water soluble lithium compound being selected from the group comprising polymeric inorganic and/or organic salts of lithium such as lithium homo- and/or copolyacrylate and/or monomeric inorganic and/or organic salts of lithium, such as lithium carbonate, lithium halides, lithium sulfates including lithium hydrogen sulfate, lithium citrate, and/or bases such as lithium hydroxide and mixtures thereof, said polymeric salt of lithium being preferably selected from acrylic homopolymers, acrylic copolymers such as copolymers of acrylic acid and maleic acid and/or acrylamide, polyphosphates and mixtures thereof, said polymeric salt of lithium being more preferably a $Li_2Na_2$polyphosphate, lithium-sodium hexamethaphosphate or lithium polyacrylate.

According to the inventive process or composition, it is especially preferred that a polymeric inorganic and/or organic salts of lithium are used as at least one water soluble lithium compound wherein preferably at least 40 mole-%, preferably 45 to 80 mole-% and more preferably 95 to 100 mole-%, of the acid sites of said polymeric salts of lithium are neutralized by lithium.

According to another preferred embodiment of the inventive process, the at least one source of a water soluble lithium compound is added to the aqueous preparation in an amount such that the total amount of solubilised lithium in the aqueous preparation is from 1500 to 2500 ppm, calculated relative to the water in the preparation.

According to the present invention, it is especially preferred that the aqueous preparation contains strains of bacteria selected from the group comprising *Methylobacteria* and *Pseudomonas* which are resistant to, tolerant to and/or degrade said aldehyde-releasing and/or aldehyde-based biocides in absence of said lithium ions, more preferably are strains of bacteria selected from the group comprising *Methylobacteria extorquens, Pseudomonas putida, Pseudomonas mendocina* or mixtures thereof, which are resistant to, tolerant to and/or degrade said aldehyde-releasing and/or aldehyde-based biocides in absence of said lithium ions.

According to another preferred embodiment of the invention, the minerals are selected from the group comprising natural calcium carbonate, synthetic, precipitated calcium carbonate, kaolin, talcum, aluminium hydroxide, aluminium silicate, titanium dioxide and mixtures thereof, and preferably comprise natural and/or synthetic calcium carbonate.

In the following, it is referred to further preferred embodiments of the present invention:

According to a preferred embodiment of the inventive composition or process, the aqueous preparation is a suspension and/or dispersion, preferably a White Mineral Dispersion (WMD).

According to yet another embodiment of the inventive composition or process, the preparation is a calcium carbonate suspension comprising ground calcium carbonate and/or precipitated calcium carbonate.

The acid sites of the polymeric lithium salt according to the present invention is preferably partially or completely neutralized by lithium or mixtures of lithium and other cations. According to one preferred embodiment of the inventive composition or process, the amount of the neutralized agent represents from about 0.1 to 2.0 wt.-%, preferably from about 0.2 to 0.9 wt.-% and most preferably from about 0.4 to 0.8 wt.-%, based on the total weight of the preparation. If a pigment suspension is present, preferably 0.02 to 0.2 mg/m$^2$ of polymeric lithium salt in respect to pigment surface are present.

According to one preferred embodiment of the inventive composition or process, the at least one source of a water soluble lithium compound is contained in the aqueous preparation in an amount such that the total amount of lithium ions in the aqueous preparation is from 1000 to 3000 ppm, calculated relative to the water in the preparation. The Li$^+$ ion content can also be added using different sources of lithium compound, such as the combination of polymeric and monomeric lithium salts, resulting in the total amount of Li$^+$ ions, calculated relative to the weight of the water in the preparation.

According to one preferred embodiment of the inventive process, the at least one source of a water soluble lithium compound to be used in an amount such that the total amount of lithium ions in the aqueous preparation is from 1000 to 3000 ppm, calculated relative to the weight of water in the preparation is selected from the group comprising polymeric lithium salts, lithium carbonate, lithium chloride, lithium fluoride, lithium bromide, lithium iodide, lithium sulfate litium hydroxid, lithium salt of carboxylic acid and mixtures thereof.

The present invention is especially suitable for providing biocidal activity in slurries or aqueous suspensions containing strains of bacteria of the genus *Pseudomonas* spp. and *Methylobacterium* spp. which are resistant to, tolerant to and/or degrade said aldehyde-releasing and/or aldehyde-based biocides in absence of said lithium ions.

When in the following more detailed description of the invention reference is made to the process of the present invention, it is to be understood that the preferred embodiments and technical details also apply to the composition and the use of a composition as defined herein and especially in the claims.

In one especially preferred embodiment of the present invention, the inventive composition comprises a specific amount of aldehyde-releasing and/or aldehyde-based biocide and a specific amount of a lithium compound for providing biocidal activity against strains of bacteria which are resistant to, tolerant to and/or degrade said aldehyde-releasing and/or aldehyde-based biocides in absence of said lithium ions in aqueous preparations. The aldehyde-releasing and/or aldehyde-based biocide and the at least one source of a water soluble lithium can be added separately (first aldehyde-releasing and/or aldehyde-based biocide and then the at least one source of a water soluble lithium or vice versa) or simultaneously (e.g. as an aqueous mixture) to the aqueous preparation. Furthermore, the aldehyde-releasing and/or aldehyde-based biocide and/or the biocidal activity effecting compound can be added once, e.g. before, during or after the manufacture of the preparation, or several times e.g. in specific time intervals. It is especially preferred to add the biocidal activity effecting compound during the storage time of the aqueous preparation once and to add the aldehyde-releasing and/or aldehyde-based biocide several times, wherein the aldehyde-releasing and/or aldehyde-based biocide can be added before the addition of the biocidal activity effecting compound, together with the biocidal activity effecting compound and/or after the addition of the biocidal activity effecting compound.

It is to be understood that the amount of aldehyde-releasing and/or aldehyde-based biocide according to the present invention is selected such that it is in combination with the lithium compound in the preparation sufficient, i.e. high enough for providing efficient biocidal activity against strains of bacteria which are resistant to, tolerant to and/or degrade said aldehyde-releasing and/or aldehyde-based biocides but at the same time is so low that no significant biocidal activity would be observed against strains of bacteria which are resistant to, tolerant to and/or degrade said aldehyde-releasing and/or aldehyde-based biocides in absence of said lithium ions. In other words, by using the inventive process or composition efficient biocidal activity is provided and huge (and thus unwanted) amounts of aldehyde-releasing and/or aldehyde-based biocides are avoided.

The composition is preferably formulated to be mixed with the aqueous preparation to be stabilized, preserved or controlled with respect to its microbial contamination in any desired ratio to achieve the desired biocidal activity.

The use of the inventive process or composition providing biocidal activity provides a number of improved properties. First of all, the inventive composition provides excellent biocidal activity when incorporated into aqueous preparations such as suspensions, dispersions or slurries of calcium carbonate, kaolin, talc and the like containing strains of bacteria which are resistant to, tolerant to and/or degrade said aldehyde-releasing and/or aldehyde-based biocides in absence of said lithium ions. Furthermore, the inventive process provides excellent properties concerning stabilization, preservation and/or control of the microbial contamination of aqueous preparations by such bacterial strains also over longer periods of time. Preferably, the composition and the inventive process provide biocidal activity (stabilization, preservation and/or control of the microbial contamination) of aqueous preparations for a time period of at least 2 days, more preferably for at least 4 days, still more preferably for at least 6 days and most preferably for a minimum of 8 days.

The addition or the use of the inventive process or compositions results in a reduced growth and accumulation of strains of bacteria which are resistant to, tolerant to and/or degrade said aldehyde-releasing and/or aldehyde-based biocides in absence of said lithium ions and the tendency of alterations of these preparations is reduced, while low viscosity, the brilliance of the colour and the odour quality of the preparations can be maintained. Furthermore, the stabilization of such preparations against attack and destruction by strains of bacteria which are resistant to, tolerant to and/or degrade said aldehyde-releasing and/or aldehyde-based biocides in absence of said lithium ions, results in a good microbiological quality of the preparations.

The biocide suitable for the present invention may be selected from the group comprising aldehyde-based biocides, aldehyde-releasing biocides and mixtures thereof.

Preferred aldehyde-releasing biocides according to the present invention include formaldehyde-releasing biocides, acetaldehyde-releasing biocides, succinaldehyde-releasing biocides, 2-propenal-releasing biocides and mixtures thereof.

The aldehyde-based biocide of the present invention is preferably a biocide selected from the group comprising formaldehyde, acetaldehyde, glyoxal, succinaldehyde, glutaraldehyde, 2-propenal, phthalic dialdehyde and mixtures thereof.

According to another embodiment of the present invention, the aldehyde-releasing compound is selected from the group comprising benzyl alcoholmono(poly)-hemiformal, ethylenglycolhemiformal, tetrahydro-1,3,4,6-tetrakis(hydroxylmethyl)imidazo[4,5-d]imidazole-2,5(1H,3H)-dione (also commonly referred to as TetraMethylolAcetyleneDiurea TMAD) and mixtures thereof.

According to yet another embodiment of the present invention, the aldehyde-releasing or aldehyde-based compound is selected from the group comprising formaldehyde, acetaldehyde, glyoxal, glutaraldehyde, 2-propenal, phthalic dialdehyde and mixtures thereof, and preferably is formaldehyde, glutaraldehyde or a mixture thereof.

According to another preferred embodiment of the present invention, the aldehyde-releasing and/or aldehyde-based biocide is used together with other biocides selected from the group consisting of 5-chloro-2-methyl-2H-isothiazolin-3-one (CIT), 2-methyl-2H-isothiazolin-3-one (MIT) and mixtures thereof.

Preferably, the aldehyde-releasing biocide in the form of a formaldehyde-releasing biocide is a biocide which is a reaction product or condensation product of formaldehyde (or formaldehyde-supplying compound) and $C_1$- to $C_{10}$-alkyl-, -aryl-, -aralkylalcohol, glycol, glycol ether, urea, urea derivatives and mixtures thereof. Also preferred are compounds with activated halogen atoms liberating formaldehyde.

Preferred aldehyde-releasing biocides of the present invention are also [1,2-Ethanediylbis(oxy)]-bis-methanol and tetramethylolacetylene diurea.

In one embodiment of the present invention, the aldehyde-releasing biocide and/or aldehyde-based biocide are in an undiluted, i.e. concentrated form. In another embodiment, the aldehyde-releasing biocide and/or aldehyde-based biocide are diluted to a suitable concentration before being added to the aqueous preparation. In the diluted form, the aldehyde-releasing biocide and/or aldehyde-based biocide is preferably dissolved in water, wherein the corresponding diluted composition comprises preferably up to 99 wt.-% of an aldehyde-releasing biocide and/or aldehyde-based biocide, based on the total weight of the composition. More preferably, the composition in water comprises 50 to 95 wt.-% of an aldehyde-releasing biocide and/or aldehyde-based biocide and most preferably 60 to 90 wt.-% of an aldehyde-releasing biocide and/or aldehyde-based biocide, based on the total weight of the composition, whereby the composition may further comprise suitable stabilizers.

In another preferred embodiment of the present invention, the aldehyde-releasing biocide comprises a mixture of at least two aldehyde-releasing biocides. In yet another preferred embodiment of the present invention, the aldehyde-based biocide comprises a mixture of at least two aldehyde-based biocides. In one preferred embodiment of the present invention a mixture of aldehyde-releasing biocides and aldehyde-based biocides is used. According to a further embodiment of the present invention, one or more aldehyde-releasing biocides and/or one or more aldehyde-based biocides are used together with other biocides, like 5-chloro-2-methyl-2H-isothiazolin-3-one (CIT) and/or 2-methyl-2H-isothiazolin-3-one (MIT). An especially preferred biocide mixture comprises glutaraldehyde, 5-chloro-2-methyl-2H-isothiazolin-3- one (CIT) and 2-methyl-2H-isothiazolin-3-one (MIT). Another especially preferred biocide mixture comprises ethylenglycolhemiformal, 5-chloro-2-methyl-2H-isothiazolin-3-one (CIT) and 2-methyl-2H-isothiazolin-3-one (MIT).

In this application glutaraldehyde and glutardialdehyde are identical. Both names are widely used in the industry.

The mixtures of aldehyde-releasing biocides and/or aldehyde-based biocides which may be used according to the present invention are dissolved in water, wherein the resulting inventive composition preferably comprise up to 99 wt.-% of aldehyde-releasing biocides and/or aldehyde-based biocides, based on the total weight of composition. More preferably, the inventive composition comprises 50 to 95 wt.-% of aldehyde-releasing biocides and/or aldehyde-based biocides and most preferably 60 to 90 wt.-% of aldehyde-releasing biocides and/or aldehyde-based biocides, based on the total weight of the composition.

The compositions to be used for the inventive process may further comprise suitable stabilizers.

In accordance with the present invention, the lithium ions are used as biocidal activity effecting compounds. The biocidal activity effecting compound referred to herein is a compound which is capable of effecting or inducing biocidal activity of the aldehyde-releasing biocide and/or aldehyde-based biocide or is capable of stabilizing the microbial properties of the aqueous preparation in comparison to a preparation having no such biocidal activity effecting compound but e.g. only one or more aldehyde-releasing and/or aldehyde-based biocides in an amount such that the total amount of aldehyde-releasing and/or aldehyde-based biocides in the aqueous preparation is from 250 ppm to 5000 ppm, calculated relative to the water in the preparation. The lithium ions, used according to the present invention in combination with aldehyde releasing biocides, prevent or reduce the growth and accumulation of strains of bacteria in aqueous preparations which are resistant to, tolerant to and/or degrade said aldehyde-releasing and/or aldehyde-based biocides in absence of said lithium ions.

In a preferred embodiment of the present invention the lithium ions are preferably added in the form of lithium salts, wherein the anionic group is preferably selected from the group comprising chloride, fluoride, bromide, iodide, carbonate, sulfate, phosphate, nitrate and mixtures thereof. In particular, lithium carbonate, lithium chloride, lithium fluoride, lithium bromide, lithium iodide, lithium sulfate and mixtures thereof are especially preferred as the biocidal activity effecting compound of the present invention. Alternatively, the lithium ions can be introduced into the aqueous preparation by adding elementary lithium or lithium hydroxide.

According to a preferred embodiment of the present invention, the aldehyde-releasing and/or aldehyde-based biocide is contained in the aqueous preparation in an amount of from 750 ppm to 4000 ppm, preferably in amount of from 1500 ppm to 3000 ppm and most preferably is in the range of 1000 ppm to 2000 ppm, calculated relative to the water in the preparation. It is further preferred that the at least one source of a water soluble lithium compound is contained in the aqueous preparation in an amount such that the total amount of lithium ions in the aqueous preparation is from 1500 to 2500 ppm or 1500 to 2000 ppm, calculated relative to the water in the preparation. The present invention is inter alia based on the finding that the combination of aldehyde-releasing and/or aldehyde-based biocide in the amount specified herein together with the water soluble lithium compound(s) in the amount specified and claimed herein allows for the efficient treatment of aqueous preparations containing bacteria which are resistant to, tolerant to and/or degrade said aldehyde-releasing and/or aldehyde-based biocides in absence of said lithium ions.

It is to be noted that the aforementioned figures reflect the amount of lithium ions being added via the source of a water soluble lithium compound to an aqueous preparation as biocidal activity effecting compound and do not cover any dissolved lithium ions which may naturally be present in the aqueous preparation. However, the amount of dissolved naturally occurring lithium ions in e.g. a calcium carbonate slurry usually is neglectable and well below 50 ppm, based on the pigment content of the slurry.

In one embodiment of the present invention, the compositions comprising one or more aldehyde-releasing and/or aldehyde-based biocides and the lithium ions as biocidal activity effecting compound are in an undiluted, i.e. concentrated form. In another embodiment the compositions comprising one or more aldehyde-releasing and/or aldehyde-based biocides and the lithium ions as biocidal activity effecting compound are diluted with water to yield a suitable concentration.

The ratios of the aldehyde-releasing biocide and/or aldehyde-based biocide and lithium ions as biocidal activity effecting compound may vary over a wide range. In the composition according to the invention, the ratio of the aldehyde-releasing and/or aldehyde-based biocide to lithium ions as biocidal activity effecting compound corresponds preferably to a weight ratio of from 10:1 to 1:10, preferably from 5:1 to 1:5, particularly preferably from 2:1 to 1:2.

According to the present invention, the compositions are used to introduce biocidal activity into aqueous preparations used in many applications, for example, in the field of paper making, paints, detergents and cosmetics. Aqueous preparations in the meaning of the present invention comprise suspensions, dispersions and slurries with a water-insoluble solid content of 1 to 85 wt.-%, preferably from 10 to 82 wt.-% and most preferably from 20 to 80 wt.-% based on the total weight of the aqueous preparation. The water-insoluble solids in the preparations according to the invention comprise natural or synthetic minerals, fillers and/or pigments based on natural or synthetic raw materials.

Typically, the aqueous preparations according to the present invention have a pH value of 6 to 10.5, preferably a pH value of 7 to 10 and a viscosity being preferably in the range between 50 to 800 mPa·s and preferably 80-600 mPa·s, as measured with a Brookfield DV-II Viscometer at a speed of 100 rpm and equipped with a LV-3 spindle.

The water-insoluble solids in the form of natural or synthetic minerals, fillers or pigments are selected from the group consisting of calcium carbonate such as ground calcium carbonate and precipitated calcium carbonate, kaolin, kaolinitic clay, calcined kaolinitic clay, talc, chalk, calcium sulfate, quartz, attapulgite, montmorillonite, diatomaceous earth, finely divided silica, aluminium oxide, aluminium hydroxide, silicates such as aluminium silicate, calcite, marble, pumice, sepiolite, dolomite, composite pigment materials including precipitated calcium carbonate, mica, titanium dioxide, and mixtures thereof.

Preferably, the composition of the present invention is incorporated into "White Mineral Dispersions" (WMD), which comprises dispersions of calcium carbonate such as ground calcium carbonate and precipitated calcium carbonate, dolomite, kaolin, kaolinitic clay, calcined kaolinitic clay and mixtures thereof.

Calcium carbonate ($CaCO_3$) e.g. is used as a coating and filling pigment, and is notably known to improve some of the optical properties of the final product, such as gloss, opacity or brightness. Calcium carbonate can be of two types: ground or natural calcium carbonate referred to as GCC, and synthetic or precipitated calcium carbonate referred to as PCC. PCC may be rhombohedral and/or scalenohedral and/or aragonitic. The GCC or PCC may additionally be surface treated, for example with fatty acids such as stearic acid and corresponding calcium salts.

Clay refers to crystalline small particles of mainly hydrous silicates of aluminum, sometimes with magnesium and/or iron substitution for all or a part of the aluminium. The main groups of clay minerals are: kaolinite, the main constituent of kaolin; halloysite; illite; montmorillonite and vermiculite. The term "kaolinitic clay" used herein refers to a soft white clay that is composed mainly of the mineral kaolinite.

Kaolin is especially used in the paper industry, which uses them to coat and fill papers and boards and improves some of the optical properties of the final product, such as gloss, opacity or brightness. However, kaolin based products include paints, agricultural compositions, fibre glass products, polymer and rubber compositions, ceramic applications, catalyst supports, pharmaceuticals, cosmetics, adhesives, filter aids, and many more.

The water-insoluble solid in the preparation may have a particle size distribution as conventionally employed for the material(s) involved in the type of product to be produced. In general, 90% of the particles will have an esd (equivalent spherical diameter as measured by the well known technique of sedimentation using Sedigraph 5100 series, Mocrometrics) of less than 5 micron. Coarse minerals, filler or pigment materials may have a particle esd generally (i.e., at least 90 wt.-%) in the range of 1 to 5 microns. Fine minerals, filler or pigment materials may have a particle esd generally less than 2 microns, e.g. 50 to 99 wt.-% less than 2 microns and preferably 60 to 90 wt.-% less than 2 microns. It is preferred that the solid particles in the preparation have a $d_{50}$ value of from 0.1 to 5 μm, preferably from 0.2 to 2 μm and most preferably from 0.35 to 1 μm, for example 0.7 μm as measured using a Sedigraph™ 5100 of Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples are dispersed using a high speed stirrer and supersonics.

For keeping mineral particles in such an aqueous preparation and thus ensuring that the viscosity of the preparation remains substantially the same over time, additives such as dispersing agents or binders are used. A suitable dispersing agent according to the present invention is preferably made of monomers and/or co-monomers selected from the group consisting of acrylic acid, methacrylic acid, itaconic acid, crotonic acid, fumaric acid, maleic anhydride acid, isocrotonic acid, aconitic acid (cis or trans), mesaconic acid, sinapinic acid, undecylenic acid, angelic acid, canellic acid, hydroxyacrylic acid, acrolein, acrylamide, acrylonitrile, dimethylaminoethyl methacrylate, vinylpyrrolidone, vinylcaprolactam, ethylene, propylene, isobutylene, diisobutylene, vinyl acetate, styrene, α-methyl styrene, methyl vinyl ketone, the esters of acrylic and methacrylic acids and mixtures thereof, wherein poly(acrylic acid) and/or poly(methacrylic acid) are preferred as dispersing agent.

The lithium ions can be introduced as biocidal activity effecting compound into the aqueous preparation via a polymeric lithium salt, like a poly(acrylic acid) and poly(methacrylic acid) having multiple acidic sites which can be partially or totally neutralised with lithium ions. The polymeric salt of lithium may be selected from $Li_2Na_2$polyphosphate, such as $Li_2Na_2P_2O_7$ and lithium polyacrylate. $Li_2Na_2$polyphosphate may be prepared by using an ion exchange technique (treatment of a cation exchanger in a column with lithium hydroxide and before passing a water based solution of $Na_4P_2O_7$ from the top to the bottom of the column).

The polymeric lithium salt which may be used as biocidal activity effecting compound according to the present invention is partially or completely neutralized, preferably to a degree of 5 to 100%, preferably to a degree of 25 to 100% and most preferably to a degree of 75 to 100% using a neutralizing agent containing ions of lithium and, optionally other alkali metals and/or alkaline earth metals. In an especially preferred embodiment the acidic sites of the polymeric lithium salt are neutralized using a neutralizing agent containing only lithium or lithium ions in combination with magnesium ions. Neutralized polyacrylates and/or polymethacrylates with an average molecular weight of not more than 50,000, preferably with an average molecular weight in the range from 1,000 to 25,000 and more preferably in the range from 3,000 to 12,000 are especially suitable.

The aqueous preparations according to the invention are highly resistant to attacks by strains of bacteria which are resistant to, tolerant to and/or degrade said aldehyde-releasing and/or aldehyde-based biocides, thus allowing problem-free handling of the products during production, storage, transport and final use.

Examples of strains of bacteria which are resistant to, tolerant to and/or degrade said aldehyde-releasing and/or aldehyde-based biocides in absence of said lithium ions which are able to grow and accumulate in the aqueous suspensions, dispersions or slurries of minerals, fillers or pigments are in particular aerobic and anaerobic bacteria species.

Examples of strains of bacteria which are resistant to, tolerant to and/or degrade said aldehyde-releasing and/or aldehyde-based biocides in absence of said lithium ions are in particular strains of the genus *Pseudomonas* spp. and *Methylobacterium* spp. Without limiting the scope of the invention, strains of the following species which are resistant to, tolerant to and/or degrade said aldehyde-releasing and/or aldehyde-based biocides in absence of said lithium ions may be mentioned: *Pseudomonas*, such as *Pseudomonas putida*, *Pseudomonas mendocina*, *Pseudomonas fluorescens*, *Pseudomonas alcaligenes*, *Pseudomonas pseudoalcaligenes*, *Pseudomonas entomophila* and *Pseudomonas syringae*; *Methylobacterium*, such as *Methylobacterium extorquens*, *Methylobacterium radiotolerants*, *Methylobacterium dichloromethanicum*, *Methylobacterium organophilum*, *Methylosinus* sp., *Hyphomicrobium zavarzinii*, *Methylosulfomonas* sp., *Methyloversatilis universalis* and *Methylococcus capsulants*.

The inventive process and the composition of the present invention comprising an aldehyde-releasing biocide and/or aldehyde-based biocide and lithium ions as biocidal activity effecting compound may especially be suitable to reduce the growth and accumulation of bacteria as described above. Furthermore, the inventive process or composition is especially suitable for treating bacteria *Pseudomonas* spp. and *Methylobacterium* spp. being typically contained in the aqueous preparations. In an especially preferred embodiment, the inventive process or composition is preferably suitable for treating strains of bacteria of the genus *Pseudomonas* spp. and *Methylobacterium* spp. which are resistant to, tolerant to and/or degrade said aldehyde-releasing and/or aldehyde-based biocides in absence of said lithium ions. The biocidal activity induced by the inventive process or composition results in a reduced growth and accumulation of microorganisms which are resistant, tolerant or degrade such biocides and thus reduces the tendency of alterations of the preparations, while a low viscosity, the brilliance of the colour and the odour quality are maintained.

The aqueous preparations according to the invention can be produced by methods known in the art, by for example, dispersing, suspending or slurring water-insoluble solids, preferably minerals, pigments or fillers, with, if appropriate, addition of a dispersing agent and, if appropriate, further additives in water.

Depending on the specific requirements and/or the respective physical and/or chemical properties of the aqueous preparation to be disinfected, the components to be used according to the invention can be applied both separately or a finished mixture may be used. In the form of a separately metered addition of the individual components of an aldehyde-releasing biocide and/or aldehyde-based biocide and lithium ions as biocidal activity effecting compound the concentration ratio may be individually adjusted depending on the present preservation problem. The aqueous preparation may be treated with the inventive composition being formulated, for example, as a customary formulation, such as, for example, a solution, an emulsion, a suspension, a powder, a foam, pastes, granules, aerosols and microencapsulations in polymeric substances.

The compositions to be used according to the invention can be incorporated into the preparations to be protected during the production of these preparations, before and/or during storage or before and/or during transport of the preparations, in a manner known by the skilled person.

One preferred embodiment of the invention refers to the use according to the invention of a mixture of (ethylenedioxy) dimethanol and at least one biocidal activity effecting lithium compound such as lithium carbonate, lithium sulphate lithium chloride and/or lithium polyacrylate for disinfecting, conservation and or control of microbial contamination in aqueous preparations. Also particularly preferred according to the invention is the use of a mixture of the aldehyde-releasing biocide (ethylenedioxy)dimethanol and at least one inventive biocidal activity effecting compound such as lithium carbonate or lithium chloride for disinfecting, conservation and or control of microbial contamination in aqueous preparations. Also particularly preferred is the use of a mixture of the aldehyde-releasing biocides and the aldehyde-based biocides glutaraldehyde and at least one inventive biocidal activity effecting compound such as lithium carbonate or lithium chloride for disinfecting, conservation and or control of microbial contamination in aqueous preparations. Especially preferred is the use of the aldehyde-releasing biocides and the aldehyde-based biocides together with other biocides such as mixtures comprising glutaraldehyde, 5-chloro-2-methyl-2H-isothiazolin-3-one (CIT) and 2-methyl-2H-isothiazolin-3-one (MIT) or ethylenglycolhemiformal, 5-chloro-2-methyl-2H-isothiazolin-3-one (CIT) and 2-methyl-2H-isothiazolin-3-one (MIT) BIT and Bronopol.

The concentrations of the inventive combination of aldehyde-releasing and/or aldehyde-based biocide and at least one source of a water soluble lithium compound to be used depend on the nature and the occurrence of the microorganisms to be controlled, the initial microbial load, and on the expected storage time of the aqueous preparations of minerals, fillers or pigments to be protected. The optimum amount to be employed within the defined ranges can be determined by preliminary tests and test series on a laboratory scale and by supplementary operational tests.

The following examples may additionally illustrate the invention, but are not meant to restrict the invention to the exemplified embodiments. The examples below show the good microbiological stability of the aqueous preparations of minerals, pigments or fillers protected with the composition according to the present invention:

EXAMPLES

In all of the following examples, the particle size distribution characteristics are measured using a Sedigraph™ 5100 of Micromeritics Instrument Corporation. The method and the instrument are known to the skilled person and are commonly used to determine grain size of fillers and pigments. The measurement is carried out in an aqueous solution of 0.1 wt % $Na_4P_2O_7$. The samples are dispersed using a high speed stirrer and supersonics.

All BET specific surface area measurements, quoted in $m^2/g$, are measured according to ISO 4652.

All Brookfield-viscosities are measured with a Brookfield DV-II Viscometer equipped with a LV-3 spindle at a speed of 100 rpm and room temperature (20±3° C.).

All biocide and lithium amounts quoted in ppm represent mg values per kilogram of water in the aqueous preparation.

All quoted bacterial counts (values are in cfu/ml) in the Tables herebelow are determined after 5 days following plate-out and in accordance with counting method described in "Bestimmung von aeroben mesophilen Keimen", Schweizerisches Lebensmittelbuch, chapter 56, section 7.01, edition of 1985, revised version of 1988.

Example 1

Preparation of Calcium Carbonate Slurries a) Calcium Carbonate Slurry 1

Calcium carbonate slurry 1 was prepared by wet grinding, in a recirculating, horizontal 1.4 liter attritor ball mill (Dyno-Mill™), a 76.1 wt.-% suspension of north-Norwegian marble having a starting esd (equivalent spherical diameter) of about 45 μm, in the presence of 0.6 wt.-%, based on the total weight of dry calcium carbonate, of a radically polymerized polyacrylic acid (MW 6000 g/Mol, polydispersity 2.6 determined by gel permeation chromatography), wherein 100 mole-% of the carboxylic acid groups are neutralized by lithium. Following grinding, the calcium carbonate in suspension had the following particle size distribution:

| Diameter (μm) | wt.-% |
|---|---|
| <2 | 90.5 |
| <1 | 60.2 |
| <0.2 | 15.0 |

The Brookfield-viscosity of the slurry was 130 mPa·s. The total soluble lithium content was 1500 ppm based on the weight of water in the slurry.

b) Calcium Carbonate Slurry 2

Calcium carbonate slurry 2 was prepared by wet grinding, in a recirculating, horizontal 1.4 liter attritor ball mill (Dyno-Mill™), a 76.4 wt.-% suspension of north-Norwegian marble having a starting esd (equivalent spherical diameter) of about 45 μm, in the presence of 0.6 wt.-%, based on the total weight of dry calcium carbonate, of a radically polymerized polyacrylic acid (MW 6000 g/Mol, polydispersity 2.6 determined by gel permeation chromatography), wherein 50 mole-% of the carboxylic acid groups are neutralized by sodium and the remaining 50 mole-% of the carboxylic acid groups are neutralized by magnesium. Following grinding, the calcium carbonate in suspension had the following particle size distribution:

| Diameter (μm) | wt.-% |
|---|---|
| <2 | 91.5 |
| <1 | 62.2 |
| <0.2 | 17.9 |

The Brookfield-viscosity of the slurry was determined as 180 mPa·s.
The following Table shows the prepared calcium carbonate slurries 1 to 2 and the content of the polymeric lithium compound neutralized by various metal ions:

| Calcium carbonate slurry | Content of polymeric lithium compound [wt.-% of dry product] | Neutralization [%] |
|---|---|---|
| Calcium carbonate slurry 1 | 0.6 | Li 100 |
| Calcium carbonate slurry 2 | 0.6 | Mg:Na 50:50 | c) Calcium Carbonate Slurry 3

Calcium carbonate slurry 3 was prepared by wet grinding, in a recirculating, horizontal 1.4 liter attritor ball mill (Dyno-Mill™), a 78.7 wt.-% suspension of north-Norwegian marble having a starting esd (equivalent spherical diameter) of about 45 μm, in the presence of 0.8 wt.-%, based on the total weight of dry calcium carbonate, of a radically polymerized polyacrylic acid (MW 6000 g/Mol, polydispersity 2.6 determined by gel permeation chromatography), wherein 50 mole-% of the carboxylic acid groups are neutralized by sodium and the remaining 50 mole-% of the carboxylic acid groups are neutralized by magnesium. Following grinding, the calcium carbonate in suspension had the following particle size distribution:

| Diameter (μm) | wt.-% |
|---|---|
| <2 | 91.4 |
| <1 | 61.8 |
| <0.2 | 17.2 |

The Brookfield-viscosity of the slurry was determined as 180 mPa·s.
This slurry was then treated using lithium carbonate, added in the form of a dry powder in an amount of 8400 ppm based on the weight of water in the slurry, to obtain a final solids of 79.5 weight %

The Brookfield-viscosity of the slurry was determined as 212 mPa·s. The total soluble lithium content was 1590 ppm based on the weight of the weight of water in the slurry.

Example 2

Biocidal Activity

The biocidal activity of various aldehyde-based or aldehyde-releasing biocides in combination with lithium ions against aldehyde-resistant/tolerant/degrading strains of various bacterial species was determined in the tests herebelow.
a) EDDM Biocide (Ethylenedioxy)dimethanol (EDDM), an aldehyde-releasing biocide, was introduced into 50 g samples of each of calcium carbonate slurry 1 and calcium carbonate slurry 2 in an amount corresponding to 1500 ppm of aldehyde-releasing EDDM biocide based on the weight of the weight of water in the slurry. In parallel, control samples of calcium carbonate slurry 1 and calcium carbonate slurry 2 were prepared in absence of EDDM.

Half of the samples of calcium carbonate slurry 1 and calcium carbonate slurry 2 were then inoculated with 1 mL of *Methylobacterium extorquens*, while the remaining samples where inoculated with 1 mL of *Pseudomonas putida*. Each of the samples was incubated at 30° C. for 72 hours. Thereafter, a 1:10 dilution in phosphate buffered saline (PBS) was plated on plate count agar (PCA). These plates were incubated at 30° C. and analysed after 5 days.

| Slurry | Li (ppm on water) | *Methylobacterium extorquens* control no biocide | *Methylobacterium extorquens* EDDM 1500 ppm on water | *Pseudomonas putida* control no biocide | *Pseudomonas putida* EDDM 1500 ppm on water |
|---|---|---|---|---|---|
| Calcium carbonate slurry 1 | 1590 ppm | $10^6$ | <100 | $10^6$ | <100 |
| Calcium carbonate slurry 2 | Negligible | $10^6$ | $3.2 \cdot 10^4$ | $10^6$ | $1.6 \cdot 10^4$ |

The results of the above table confirm that the *Methylobacterium extorquens* and *Pseudomonas putida* strains employed for the tests show resistance to EDDM biocide when this biocide is implemented alone at the listed amount. The results also show that when lithium is provided alone at the listed amount, it fails to act as a biocide. It is only when EDDM is implemented in combination with lithium, in the listed amounts, that the bacterial count of the suspension falls to below $10^4$ cfu/ml.
b) EDDM Biocide Mixture An aqueous aldehyde-releasing biocide mixture containing about 85 to 95 wt.-% of EDDM, and about 0.9 to 1.1 wt.-% of 5-chloro-2-methyl-2H-isothiazolin-3-one and N-methyl-isothiazolinone (in a weight ratio of 5-chloro-2-methyl-2H-isothiazolin-3-one:N-methyl-isothiazolinone of 3:1), which represents a typical biocide mixture implemented in industry, was introduced into 50 g samples of each of calcium carbonate slurry 1 and calcium carbonate slurry 2 in an amount corresponding to 750 ppm aldehyde-releasing biocide mixture based on the weight of water in the slurry. In parallel, a control sample of calcium carbonate slurry 1 was prepared in absence of the EDDM biocide mixture.

All of samples were then inoculated twice with 1 mL of *Methylobacterium extorquens*. After each inoculation, the samples were incubated at 30° C. for 72 hours. Thereafter, a 1:10 dilution in phosphate buffered saline (PBS) was plated on plate count agar (PCA). These plates were incubated at 30° C. and analysed after 5 days.

| | Calcium carbonate slurry 1 | Calcium carbonate slurry 2 | Calcium carbonate slurry 1 |
|---|---|---|---|
| Biocide (ppm on water) | 0 ppm | 750 ppm | 750 ppm |
| Li (ppm on water) | 1500 ppm | negligible | 1500 ppm |
| Inoculation 1 | $10^6$ | $10^6$ | $2 \cdot 10^2$ |
| Inoculation 2 | $10^6$ | $10^6$ | $1.2 \cdot 10^3$ |

The results of the above table confirm that the *Methylobacterium extorquens* strain employed for the tests shows resistance to the EDDM biocide mixture when this biocide mixture is implemented alone at the listed amount. The results also show that when lithium is provided alone at the listed amount, it fails to act as a biocide. It is only when the EDDM biocide mixture is implemented in combination with lithium, in the listed amounts, that the bacterial count of the suspension falls to below $10^4$ cfu/ml.

c) Gluteraldehyde Biocide Mixture

An aqueous aldehyde-based biocide mixture containing about 20 to 23 wt.-% of aldehyde-glutaraldehyde, and about 1.15 to 1.65 wt.-% of 5-chloro-2-methyl-2H-isothiazolin-3-one (CIT), 2-methyl-2H-isothiazolin-3-one (MIT) (in a weight ratio of CMIT:MIT of 3:1), which represents a typical biocide mixture implemented in industry, was introduced into 50 g samples of calcium carbonate slurry 1 and calcium carbonate slurry 2 in an amount corresponding to 1350 ppm of aqueous aldehyde-based biocide mixture based on the weight of water in the slurry. In parallel, a control sample of calcium carbonate slurry 1 and of calcium carbonate slurry 2 were prepared in absence of the aqueous aldehyde-based biocide mixture.

All of samples were then inoculated twice with 1 mL of *Pseudomonas mendocina*. After each inoculation, the samples were incubated at 30° C. for 72 hours. Thereafter, a 1:10 dilution in phosphate buffered saline (PBS) was plated on plate count agar (PCA). These plates were incubated at 30° C. and analysed after 5 days.

|  | Calcium carbonate slurry 2 | Calcium carbonate slurry 2 | Calcium carbonate slurry 1 | Calcium carbonate slurry 1 |
|---|---|---|---|---|
| Biocide (ppm on water) | 0 ppm | 1350 ppm | 0 ppm | 1350 ppm |
| Li (ppm on water) | negligible | negligible | 1500 ppm | 1500 ppm |
| Inoculation 1 | $10^6$ | $10^6$ | $10^5$ | <100 |
| Inoculation 2 | $10^6$ | $10^6$ | $10^5$ | <100 |

The results of the above table confirm that the *Pseudomonas mendocina* strain employed for the tests shows resistance to the glutaraldehyde biocide mixture when this biocide mixture is implemented alone at the listed amount. The results also show that when lithium is provided alone at the listed amount, it fails to act as a biocide. It is only when the glutaraldehyde biocide mixture is implemented in combination with lithium, in the listed amounts, that the bacterial count of the suspension consistently falls to below $10^4$ cfu/ml, even after 2 inoculations.

d) EDDM Biocide Mixture

An aqueous aldehyde-releasing biocide mixture containing about 85 to 95 wt.-% of EDDM, and about 0.9 to 1.1 wt.-% of 5-chloro-2-methyl-2H-isothiazolin-3-one and N-methyl-isothiazolinone (in a weight ratio of 5-chloro-2-methyl-2H-isothiazolin-3-one: N-methyl-isothiazolinone of 3:1), which represents a typical biocide mixture implemented in industry, was introduced into 50 g samples of calcium carbonate slurry 1, 2 and 3 in an amount corresponding to 750 ppm of aldehyde-releasing ethylenglycolhemiformal biocide based on the weight of water in the slurry. In parallel, a control sample of calcium carbonate slurry 1, 2 and 3 were prepared in absence of the ethylenglycolhemiformal biocide mixture.

All of samples were then inoculated three times with 1 mL of *Pseudomonas putida*. After each inoculation, the samples were incubated at 30° C. for 72 hours. Thereafter, a 1:10 dilution in phosphate buffered saline (PBS) was plated on plate count agar (PCA). These plates were incubated at 30° C. and analysed after 5 days.

|  | Calcium carbonate slurry 2 | | Calcium carbonate slurry 3 | | Calcium carbonate slurry 1 | |
|---|---|---|---|---|---|---|
|  | Biocide (ppm on water) | | | | | |
|  | 0 ppm | 750 ppm | 0 ppm | 750 ppm | 0 ppm | 750 ppm |
|  | Li (ppm on water) | | | | | |
|  | negligible | negligible | 1590 ppm | 1590 ppm | 1500 ppm | 1500 ppm |
| Inoculation 1 | $10^6$ | $10^6$ | $10^5$ | <100 | $10^6$ | 500 |
| Inoculation 2 | $10^6$ | $10^6$ | $10^6$ | <100 | $10^6$ | 200 |
| Inoculation 3 | $10^6$ | $10^6$ | $10^6$ | <100 | $10^6$ | <100 |

The results of the above table confirm that the *Pseudomonas putida* strain employed for the tests shows resistance to the EDDM biocide mixture when this biocide mixture is implemented alone at the listed amount. The results also show that when lithium is provided alone at the listed amount, it fails to act as a biocide. It is only when the EDDM biocide mixture is implemented in combination with lithium, in the listed amounts, that the bacterial count of the suspension consistently falls to below $10^4$ cfu/ml, even after 3 inoculations.

e) Glutaraldehyde Biocide Mixture

An aqueous aldehyde-based biocide mixture containing about 20 to 23 wt.-% of aldehyde-glutaraldehyde, and about 1.15 to 1.65 wt.-% of 5-chloro-2-methyl-2H-isothiazolin-3-one (CIT), 2-methyl-2H-isothiazolin-3-one (MIT) (in a weight ratio of CMIT:MIT of 3:1), which represents a typical biocide mixture implemented in industry, was introduced into 50 g samples of calcium carbonate slurry 1, 2 and 3 in an amount corresponding to 1350 ppm of aldehyde-based glutaraldehyde biocide based on the weight of the weight of water in the slurry. In parallel, control samples of calcium carbonate slurry 1, 2 and 3 were prepared in absence of the glutaraldehyde biocide mixture.

All of samples were then inoculated three times with 1 mL of *Pseudomonas mendocina*. After each inoculation, the samples were incubated at 30° C. for 72 hours. Thereafter, a 1:10 dilution in phosphate buffered saline (PBS) was plated on plate count agar (PCA). These plates were incubated at 30°
C. and analysed after 5 days.

| | Calcium carbonate slurry 2 | | Calcium carbonate slurry 3 | | Calcium carbonate slurry 1 | |
|---|---|---|---|---|---|---|
| | \multicolumn{6}{c}{Biocide (ppm on water)} | | | | | |
| | 0 ppm | 1350 ppm | 0 ppm | 1350 ppm | 0 ppm | 1350 ppm |
| | \multicolumn{6}{c}{Li (ppm on water)} | | | | | |
| | negligible | negligible | 1590 ppm | 1590 ppm | 1500 ppm | 1500 ppm |
| Inoculation 1 | $10^6$ | $10^5$ | $10^5$ | <100 | $10^6$ | 500 |
| Inoculation 2 | $10^6$ | $10^5$ | $10^6$ | <100 | $10^6$ | 200 |
| Inoculation 3 | $10^6$ | $10^6$ | $10^6$ | <100 | $10^6$ | <100 |

The results of the above table confirm that the *Pseudomonas mendocina* strain employed for the tests shows resistance to the glutaraldehyde biocide mixture when this biocide mixture is implemented alone at the listed amount. The results also show that when lithium is provided alone at the listed amount, it fails to act as a biocide. It is only when the glutaraldehyde biocide mixture is implemented in combination with lithium, in the listed amounts, that the bacterial count of the suspension consistently falls to below $10^4$ cfu/ml, even after 3 inoculations.

The invention claimed is:

1. A composition comprising:
   (a) an aqueous preparation comprising at least one mineral comprising calcium carbonate,
   (b) one or more aldehyde-releasing and/or aldehyde-based biocides in an amount such that the total amount of aldehyde-releasing and/or aldehyde-based biocides in the aqueous preparation is from 250 ppm to 5000 ppm, calculated relative to the weight of water in the preparation, and
   (c) at least one source of a water soluble lithium compound in an amount such that the total amount of solubilized lithium in the aqueous preparation is from 1000 to 3000 ppm, calculated relative to the weight of water in the preparation, wherein the at least one water soluble lithium compound is selected from the group consisting of a polymeric lithium salt, $Li_2,Na_2$polyphosphate, lithium sodium hexametaphosphate, lithium polyacrylate, lithium carbonate, a lithium halide, lithium hydroxide, a lithium sulfate, lithium hydrogen sulfate, lithium citrate, and any mixture thereof.

2. The composition according to claim 1, wherein the one or more aldehyde-releasing and/or aldehyde-based biocides is an aldehyde-releasing compound selected from formaldehyde-releasing biocides, acetaldehyde-releasing biocides, succinaldehyde-releasing biocides, 2-propenal-releasing biocides, and mixtures thereof.

3. The composition according to claim 1, wherein the one or more aldehyde-releasing and/or aldehyde-based biocides is a formaldehyde-releasing biocide selected from benzyl alcoholmono(poly)-hemiformal, ethylenglycolhemiformal, tetrahydro-1,3,4,6-tetrakis(hydroxylmethyl)imidazo[4,5-d] imidazole-2,5(1H,3H)-dione, (TetraMethylolAcetyleneDiurea TMAD), and mixtures thereof.

4. The composition according to claim 1, wherein the one or more aldehyde-releasing and/or aldehyde-based biocides is an aldehyde-based biocide selected from formaldehyde, acetaldehyde, glyoxal, glutaraldehyde, 2-propenal, phthalic dialdehyde, and mixtures thereof.

5. The composition according to claim 1, wherein the one or more aldehyde-releasing and/or aldehyde-based biocides is an aldehyde-based biocide selected from formaldehyde, glutaraldehyde or a mixture thereof.

6. The composition according to claim 1, wherein the aldehyde-releasing and/or aldehyde-based biocide is included in the composition with another biocide selected from 5-chloro-2-methyl-2H-isothiazolin-3-one (CIT), 2-methyl-2H-isothiazolin-3-one (MIT), and mixtures thereof.

7. The composition according to claim 1, wherein the at least one water soluble lithium compound is a polymeric lithium salt is a homopolymer and/or copolymer of acrylic acid.

8. The composition according to claim 1, wherein the at least one water soluble lithium compound is lithium chloride, lithium carbonate, lithium hydroxide, or any mixture thereof.

9. The composition according to claim 1, wherein the at least one water soluble lithium compound is lithium carbonate, a lithium halide, a lithium sulfate, lithium hydrogen sulfate, lithium citrate, and any mixture thereof.

10. The composition according to claim 1, wherein the at least one water soluble lithium compound is a polymeric lithium salt selected from a lithium salt of an acrylic acid homopolymer, a lithium salt of an acrylic copolymer, a lithium salt of a copolymer of acrylic acid and maleic acid and/or acrylamide, a lithium salt of a polyphosphate, or any mixture thereof.

11. The composition according to claim 1, wherein the at least one water soluble lithium compound is a $Li_2Na_2$polyphosphate, lithium-sodium hexametaphosphate or lithium polyacrylate.

12. The composition according to claim 1, wherein the at least one water soluble lithium compound is a polymeric lithium salt in which at least 40 mole-% of acid sites of the polymeric lithium salt are neutralized by lithium.

13. The composition according to claim 1, wherein the at least one water soluble lithium compound is a polymeric lithium salt in which 40 to 80 mole-% of acid sites of the polymeric lithium salt are neutralized by lithium.

14. The composition according to claim 1, wherein the at least one water soluble lithium compound is a polymeric lithium salt in which 95 to 100 mole-% of acid sites of the polymeric lithium salt are neutralized by lithium.

15. The composition according to claim 1, wherein the mineral comprises calcium carbonate and one or more of kaolin, talcum, aluminium hydroxide, aluminium silicate, and titanium dioxide.

16. The composition according to claim 1, wherein the mineral comprises natural and/or precipitated calcium carbonate.

* * * * *